United States Patent [19]

Rhodes et al.

[11] Patent Number: 4,896,465
[45] Date of Patent: Jan. 30, 1990

[54] RETAINER APPARATUS

[76] Inventors: Robert Rhodes, 309 W. 550 North Cir., St. George, Utah 84770; Dennis R. Hauze, 910 Millstream, Bountiful, Utah 84010

[21] Appl. No.: 273,194

[22] Filed: Nov. 18, 1988

Related U.S. Application Data

[62] Division of Ser. No. 89,866, Aug. 27, 1987, abandoned.

[51] Int. Cl.⁴ .............................................. A61B 17/12
[52] U.S. Cl. ...................... 51/391; 51/181 R; 128/849; 248/74.2; 248/205.2; 269/275; 269/286
[58] Field of Search ............... 269/328, 274, 275, 286; 128/304, 346; 248/65, 74.1, 74.2, 205.2; 156/293, 294, 303.1; 51/181 R, 211 R, 388, 391

[56] References Cited

U.S. PATENT DOCUMENTS

| | | | |
|---|---|---|---|
| 2,515,091 | 7/1950 | May | 51/181 |
| 2,519,661 | 8/1950 | Johnson | 269/275 |
| 2,727,325 | 12/1955 | Jurinic | 265/275 |
| 2,757,665 | 8/1957 | Tanikawa | 128/346 |
| 2,760,217 | 8/1956 | McKenzie | 51/181 |
| 2,796,787 | 6/1957 | Aske | 269/274 |
| 3,020,041 | 2/1962 | Peterson | 269/275 |
| 3,286,963 | 11/1966 | Bergman | 248/74.2 |
| 3,449,008 | 6/1969 | Colechia | 269/275 |
| 3,606,218 | 9/1971 | Enlund | 248/74.2 |
| 3,630,195 | 12/1971 | Santomieri | 128/133 |
| 3,837,633 | 9/1971 | Paulsen | 269/275 |
| 3,866,611 | 2/1975 | Baumrocker | 128/346 |
| 4,027,866 | 6/1977 | Ruggiero | 269/274 |
| 4,079,478 | 3/1978 | Andrews, Sr. | 128/346 |
| 4,390,019 | 6/1983 | LeVeen | 128/346 |
| 4,489,725 | 12/1984 | Casey | 128/346 |
| 4,543,751 | 10/1985 | Atikhan | 51/181 R |
| 4,807,404 | 2/1989 | Lewis | 51/391 |

Primary Examiner—Merrell C. Cashion, Jr.
Attorney, Agent, or Firm—J. Winslow Young

[57] ABSTRACT

A retainer for releasably securing devices or objects of nonuniform configuration. Clamping action is supplied by a pair of resilient synthetic sponges mounted between a pair of supports. The supports can be either hinged relative to each other or in fixed spatial relationship. A mounting means is provided for mounting the retainer to a third object such as a pole, wrist, surgical tray, drape, wall, or the like, and can include an adhesive surface or a flexible or even elastic strap.

24 Claims, 2 Drawing Sheets

RETAINER APPARATUS

This application is a Division of Ser. No. 07/089,866, filed Aug. 27, 1987, now abandoned.

FIELD OF THE INVENTION

This invention relates to retainers and, more particularly to a retainer apparatus and method wherein two layers of resilient material such as a synthetic foam are retained between supports to provide the clamping action for devices and tubing, even devices and tubing having nonuniform profiles.

THE PRIOR ART

Health care professionals, doctors and nurses, are continually confronted with the need to releasably secure various devices or other items of equipment used in their professional activities. Securement of these devices such as tubing and surgical instruments including cauterizing implements is particularly important since several sizes of tubing, for example, will be used to carry various fluids to and from a patient. Keeping the several types of tubing properly aligned and oriented is critical since an inadvertent infusion of a fluid into the wrong tubing could result in death to a patient. Further the clutter of tubing could unduly hamper the health care professional in her or his care of a patient particularly in an emergency situation.

Another area of concern is in the operating suite where great care is taken to assure that there is strict segregation of sterile devices from the nonsterile surroundings. For example, a surgeon using a cauterizing instrument is continually concerned with the inadvertent loss of the scalpel from the sterile field. Frequently, the weight of the electrical cord pulls the scalpel off the sterile field. This means that valuable surgery time must be spent in securing the cauterizing scalpel to the sterile field and subsequently releasing the sam for repeated usages. There are no suitable devices readily available so that the surgeon is required to improvise using various clamping forceps as the securement device for engaging the cauterizing scalpel to the sterile field.

The foregoing examples are merely illustrative of the need for a versatile clamping apparatus and method whereby various sizes, numbers, and shapes of devices can be releasably secured in any suitable configuration.

It would, therefore, be an advancement in the art to provide a retainer apparatus and method for releasably securing one or more devices at a predetermined location. It would also be an advancement in the art to provide a retainer apparatus and method for releasably securing one or more devices having nonuniform configurations and sizes. Such a novel retainer apparatus and method is disclosed and claimed herein.

BRIEF SUMMARY OF OBJECTIVES OF THE INVENTION

The present invention is a novel retainer apparatus and method whereby two layers of a resilient medium such as synthetic foam material are mounted between supports. The resilience of the foam material supplies the desired degree of clamping action upon the device or devices held between the two layers of synthetic foam material. The supports may be slightly resilient or joined along a hinge so as to assist the placement of devices between the layers of resilient foam material. An engagement system may be included to pull the supports slightly together to partially compress the layers of foam about the device. Various basal configurations are available as well as various securement systems for securing the base to suitable places such as a pole, an arm, or a surface.

It is, therefore, a primary object of this invention to provide improvements in retainer apparatus.

It is another object of this invention to provide improvements in the method of retaining devices of various configurations and sizes.

Another object is to provide a resilient media so as to releasably hold a device through the clamping mechanism of the resilient media.

Another object is to provide a retainer with a variety of basal configurations to accommodate selectively engaging the retainer to a predetermined structure or surface.

These and other objects and features of the present invention will become more readily apparent with reference to the drawing and accompanying description taken in conjunction with the appended claims.

DETAILED DESCRIPTION OF THE PREFERRED EMBODIMENTS

Figure 1:
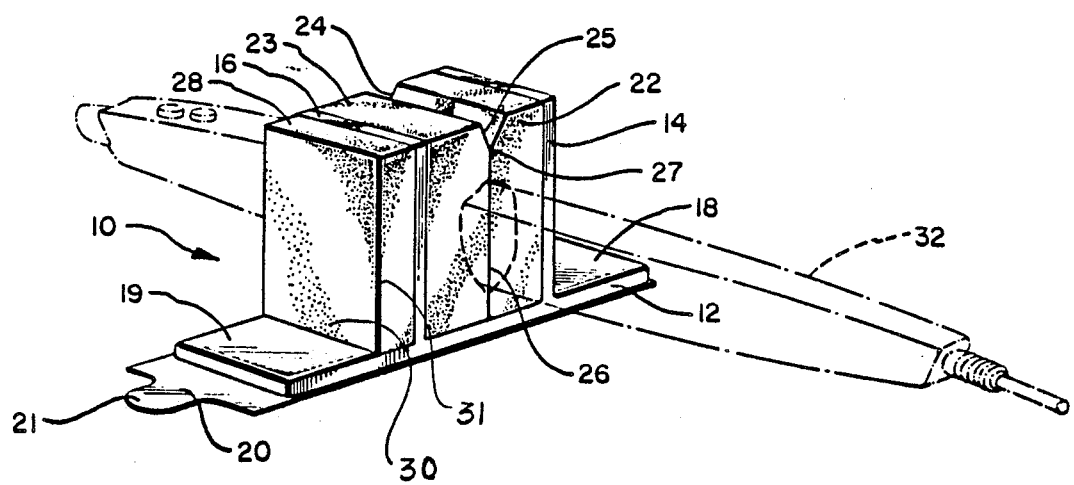
FIG. 1 is a perspective view of a first preferred embodiment the novel retainer of this invention shown holding a cauterizing instrument (shown in broken lines to more clearly illustrate the environment)

The invention is best understood from the following detailed description with reference to the drawing wherein like parts are designated with like numerals throughout.

General Discussion

Certain synthetic sponges such as those fabricated from a polyurethane, for example, can be fabricated with a predetermined range of resilience and cell size. Cell configurations in these sponges range between closed cells wherein each cell is a closed bubble and reticulated sponges wherein the interconnecting fibrous membranes between the original cells are all structure that remains with any combination between these two extremes.

Importantly, the synthetic sponge material is selected with the desired degree of resiliency so as to readily conform to various devices having nonuniform shapes without crushing the device. The sponge also provides frictional resistance against slippage of the device. Sponge materials are readily available commercially and may be obtained in any desired degree of resiliency, cell size, color, etc. and can be cut into any one of a myriad of shapes. Importantly, particularly for the medical applications envisioned for the retainer of this invention, these synthetic sponges can also be subjected to a suitable sterilizing process.

The Preferred Embodiments

Referring now more particularly to FIG. 1, the novel retainer of this first preferred embodiment of this invention is shown generally at 10 and includes a base 12 with upright flanges 14 and 16 extending perpendicularly therefrom. Flanges 14 and 16 support sponges 22 and 23, respectively, and can be either rigid or fabricated so as to include a desired degree of resiliency to allow being spread apart slightly to admit larger devices therebetween while also assisting in the clamping action provided by sponges 22 and 23. Flanges 14 and 16 are fabricated integral with base 12 to provide the overall support structure to retainer 10. This support structure can be fabricated from extruded plastic, aluminum, or the like, or may be injection molded with plastic.

Base 12 also includes a pair of extensions 18 and 19 extending beyond flanges 14 and 16, respectively, to provide additional support surface for base 12. Base 12 is configured to be adhesively secured to a surface such as a sterile drape (not shown) in the surgical suite, an equipment rack (not shown), and the like. A protective cover 20 having a tab 21 removably secured thereto protects the adhesive surface on the bottom of base 12. This is conventional technology, well known in the art. Clearly, alternate attachment means for base 12 can be incorporated into retainer 10 such as the other attachment devices shown in conjunction with the other embodiments of this invention disclosed and described relative to FIGS. 3-5 herein.

Sponges 22 and 23 are configured a blocks of synthetic sponge material and are mounted between flanges 14 and 16 with the abutting faces of sponges 22 and 23 forming a slot 26 into which an item is inserted and thereby clamped by retainer 10. Preferably, sponges 22 and 23 are adhesively mounted to the respective surfaces of base 12 and flanges 14 and 16 so as to preclude inadvertent dislodgement of sponges 22 and 23. The corners of sponges 22 and 23 are cut to form bevels 24 and 25, respectively, which cooperate to form a notch 27. Notch 27 forms the entry to slot 26 thereby facilitating the placement of objects into retainer 10.

Insertion of a device, for example cauterizing instrument 32 (shown by broken lines) is done by bringing scalpel 32 downwardly into notch 27 and slot 26 upon displacing sponges 22 and 23 outwardly until instrument 32 is suitably located in slot 26. The relationship of instrument 32 to retainer 10 is illustrated schematically by the broken lines.

A relatively thin block of sponge, sponge 28, is mounted to the outer face of flange 16 and has an outer layer of abrasive or grit 30. Abrasive 30 is provided as a mechanism for scraping or otherwise cleaning instruments such as cauterizing instrument 32 which become clogged or otherwise coated with coagulated and scorched blood, tissue, and the like. A scraping edge 31 is included to assist in the removal of accumulated debris from the blade of instrument 32.

The surgeon uses retainer 10 to hold instrument 32 during periods when he is using other surgical equipment (not shown). Instrument 32 is easily retrieved by being removed from retainer 10 by being pulled upwardly or outwardly to release it from slot 26. Periodically the surgeon or assistant scrapes the blade of cauterizing instrument 32 against abrasive 30 or scraping edge 31 to clean the blade thus allowing the surgeon to continue the surgical procedure with a cleaned instrument. Advantageously, retainer 10 is securely mounted to the desired surface whether a surgical drape, equipment stand, instrument tray, or the like, (not shown) so that retainer 10, and also abrasive 30, is securely held so as to permit one hand operation of instrument 32 during the clamping, removal, and cleaning processes.

Figure 2:
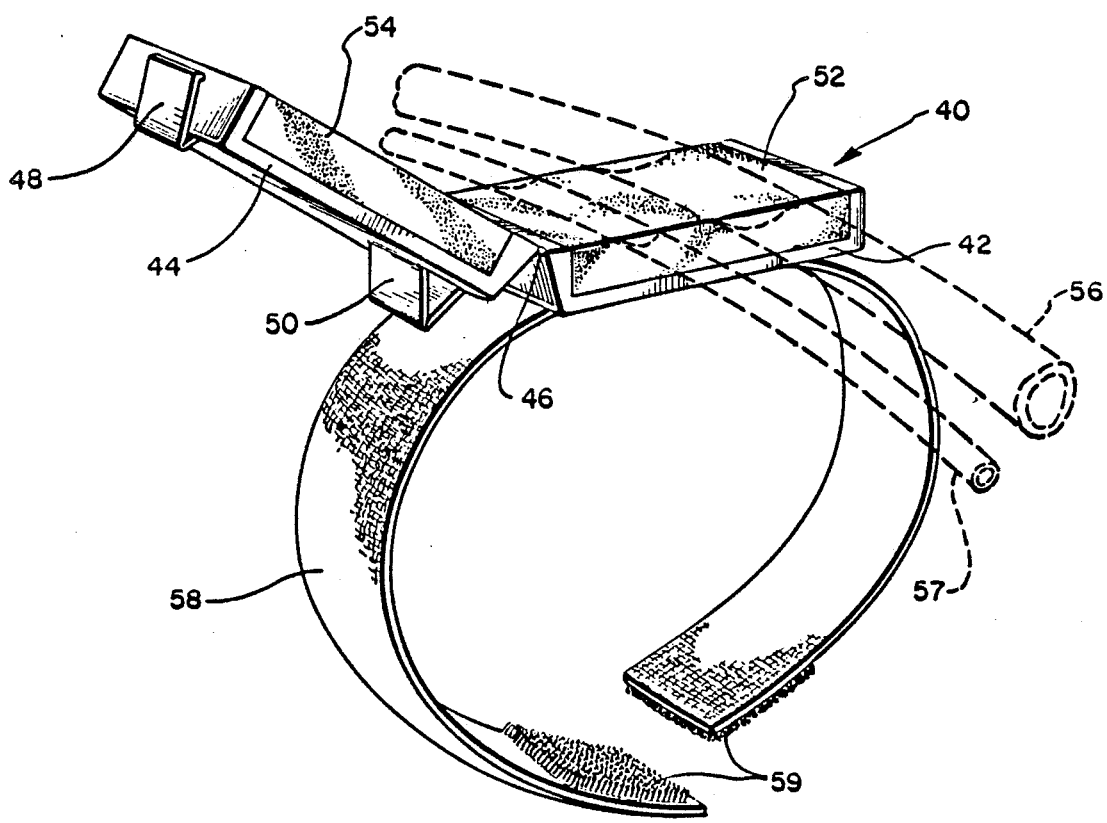
FIG. 2 is a perspective view of a second preferred embodiment of the novel retainer of this invention shown open and in juxtaposition with tubing (shown in broken lines)
Figure 3:
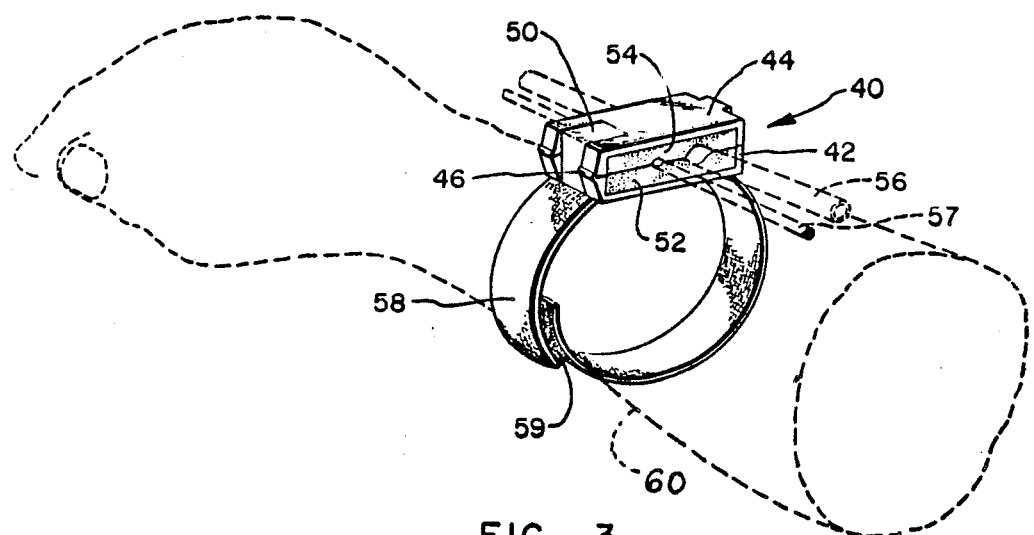
FIG. 3 is a perspective view of the retainer shown in FIG. 2, the retainer being closed (the retainer also shown secured to wrist shown in broken lines)

Referring now more particularly to FIGS. 2 and 3, a second preferred embodiment of the retainer of this invention is shown generally at 40 and includes a pair of brackets 42 and 44 hingedly joined together along a hinge 46. A detent 48 on the end of bracket 44 provides a gripping element to assist the user in opening retainer 40. A similar detent is also found on the corresponding end of bracket 42 but is hidden in the particular perspective view of retainer 40 shown by FIGS. 2 and 3.

A spring 50 is fabricated into brackets 42 and 44 during manufacture so as to resiliently urge brackets 42 and 44 into either the fully open configuration shown in FIG. 2 or the fully closed configuration shown in FIG. 3. This type of spring is well known in the art and is found in numerous applications primarily in stoppers for liquids dispensing caps such as found on bottles of shampoo, liquid soap, and the like.

Brackets 42 and 44 are configured as open channels with blocks of sponge 52 and 54, respectively, secured therein so that when retainer 40 is closed sponges 52 and 54 are brought into juxtaposition with the selected object or objects clamped therebetween. In this instance the objects are tubing 56 and 57 (shown in broken lines). Tubing 56 is shown as larger in diameter than tubing 57 so as to clearly illustrate one of the novel features of this invention in that nonuniform sizes of objects can be clamped by the resilient nature of sponges 52 and 54.

Retainer 40 includes a strap 58 with a fastener 59 to accommodate securement of retainer 40 to a wrist 60 (shown in broken lines) or other suitable object (not shown). In this instance, fastener 59 is fabricated from a commercially available fastener sold under the trade name of Velcro so as to allow strap 58 to be releasably secured about any suitable object. Alternatively, retainer 40 could be configured with the adhesive system shown on base 12 of retainer 10 (FIG. 1) eliminating entirely the requirement for strap 58.

However, in this presently preferred embodiment illustrated in FIGS. 2 and 3 strap 58 serves to releasably secure retainer 40 to wrist 60 so that tubing 56 and 57 can be securely held relative to wrist 60. Advantageously, closure of brackets 42 and 44 causes sponges 52 and 54 to be resiliently compressed about tubing 56 and 57 thereby frictionally engaging tubing 56 and 57 securely without crushing of tubing 56 and 57. Further, the nature of sponges 52 and 54 is such that they frictionally engage tubing 56 and 57 to resist pulling of tubing 56 or 57 through retainer 40.

Replacement of tubing 56 or 57 is accomplished easily by the operator (not shown) simply releasing detent 48 and opening brackets 42 and 44 against the spring action of spring 50 until in the fully opened position shown in FIG. 2. Thereafter, brackets 42 and 44 are again closed by being brought into juxtaposition and detent 48 is again engaged to secure retainer 40.

Figure 4:
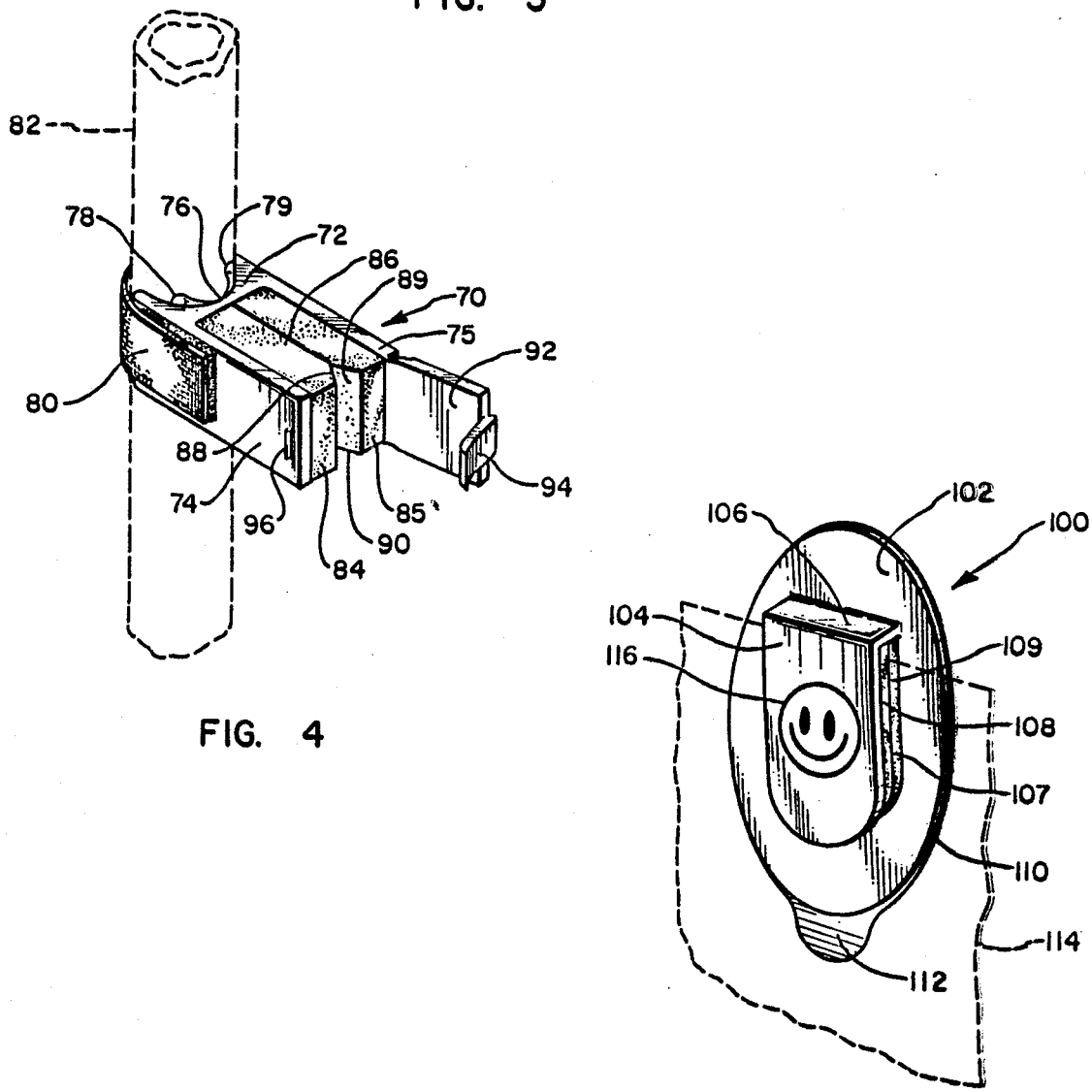
FIG. 4 is a perspective view of a third preferred embodiment of the novel retainer of this invention (shown in the environment of a pole, illustrated in broken lines)

Referring now more particularly to FIG. 4, a third preferred embodiment of the novel retainer apparatus of this invention is shown generally at 70 and includes a bracket member 72 with a pair of arms 74 and 75 extending outwardly therefrom. Bracket 72 is configurated with a curvilinear profile 76 on a portion of bracket 72 opposite arms 74 and 75 so as to accommodate securement of retainer 70 to a pole, bed frame, or the like. A pair of raised ridges 78 and 79 on profile 76 adapt retainer 70 to attachment to a pole having a cross sectional shape of almost any configuration ranging from circular to polygonal.

A strap 80 is mounted to bracket 72 adjacent arm 75 and is adapted to be releasably engaged to arm 74 upon being secured about a pole 82 (shown in broken lines). Strap 80 is secured to arm 74 by a commercially available hook and eye fabric fastener commonly referred to by the trademark Velcro. Advantageously, the length of strap 80 is of sufficient length to accommodate engagement about a pole 82 of any suitable dimension to thereby securely engage retainer 70 thereto. Additional securement versatility may be obtained by fabricating strap 80 from an elastic material so as to apply a suitable constrictive force about pole 82.

Arms 74 and 75 extend outwardly and support sponges 84 and 85, respectively, with a slot 86 formed therebetween. A notch 90 is formed by bevelled corners 88 and 89 on the facing corners of sponges 84 and 85, respectively. Notch 90 facilitates placement of an object (not shown) similar to tubing 56 and 57 (FIGS. 2 and 3) into slot 86.

Arms 74 and 75 are sufficiently resilient to accommodate a limited degree of flexure so as to further adapt retainer 70 to receive larger sizes or irregular shapes of objects therebetween. A keeper 92 is hingedly joined to the end of arm 75 and includes a clip 94 which is adapted to releasably engage a detent 96 on the end of arm 74 when keeper 92 is closed across the ends of arms 74 and 75.

Figure 5:
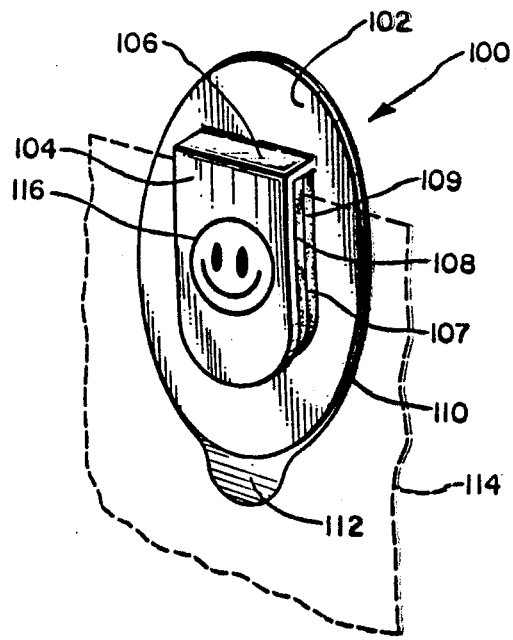
FIG. 5 is a perspective view of a fourth preferred embodiment of the novel retainer of this invention shown supporting a single sheet (shown in broken lines).

Referring now to FIG. 5, a fourth preferred embodiment of the retainer of this invention is shown at 100 and includes a base 102 with a clip 104 spaced from and essentially parallel to base 102. The distance between base 102 and clip 104 is selectively predetermined by the height of a riser 106 so as to receive two layers of sponge 108 and 109 between clip 104 and base 102.

Base 102 is larger than clip 104 so as to provide sufficient surface area for an adhesive surface 110 on the reverse face thereof to provide the desired degree of adhesive strength to retain retainer 100 at the desired location. A cover 112 is removably mounted over adhesive 110 so as to protect adhesive 100 until it is desired to adhesively secure retainer 100 to the predetermined location at which time cover 112 is removed and retainer 100 is relatively permanently attached to a surface.

The configuration of retainer 100 differs from that shown in FIGS. 2-4 in that retainer 100 is designed to be more or less permanently mounted at a fixed location whereas the other embodiments of this invention shown in FIGS. 2-4 ar designed to be removably secured in the various locations.

Sponges 108 and 109 form a slot 107 therebetween which engagedly receives an object such as chart 114 (shown in broken lines). Retainer 100 is primarily designed for holding such sheet-like items such as X-ray films, charts, posters, and the like.

A novelty design 116 or other suitable logo or aesthetic design may be affixed to the face of clip 104 to the entertainment or education of the observer. This feature can also be included on any of the retainers of FIGS. 1-4. For example, if the particular retainer is intended to be used in a pediatric setting design 116 can be of the pleasing feature shown. Further, design 116 could be in the form of a base relief of a popular cartoon character so as to alleviate the fear and anxiety of the pediatric patient.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A retainer comprising:
   a first support member;
   a first resilient member mounted to said first support member said first support member including an abrasive member;
   a second support member;
   a second resilient member; mounted to said second support member; and
   a base for supporting said first support member in a spaced relationship to said second support member with said first resilient member in juxtaposition with said second resilient member.

2. The retainer defined in claim 1 wherein said first support member includes the abrasive member mounted to said first support member opposite said first resilient member.

3. The retainer defined in claim 2 wherein said abrasive member is resiliently supported on said first support member by being mounted thereto by a third resilient member.

4. The retainer defined in claim 2 wherein said abrasive member comprises at least one sharp edge against which articles can be scraped.

5. The retainer defined in claim 2 wherein said abrasive member comprises a grit surface.

6. The retainer defined in claim wherein said first support member includes an engagement means for engaging said first support member to said second support member at a position spaced from said base.

7. The retainer defined in claim 6 wherein said engagement means includes constriction means for pulling said first support member and said second support member together an incremental distance.

8. The retainer defined in claim 1 wherein said first resilient member and said second resilient member comprise a synthetic foam material.

9. The retainer defined in claim 8 wherein said synthetic foam material comprises a open-cell synthetic foam.

10. The retainer defined in claim 1 wherein said first resilient member and said second resilient member each include a cooperating bevel which forms a notch to accommodate introduction of an article between said first resilient member and said second resilient member.

11. The retainer defined in claim 1 wherein said base is formed as an integral unit with said first support member and said second support member.

12. The retainer defined in claim 11 wherein said base includes a securement means for releasably securing said base to a structure.

13. The retainer defined in claim 12 wherein said securement means comprises a flexible strap.

14. The retainer defined in claim 13 wherein said flexible strap is fabricated from an elastic material.

15. The retainer defined in claim 11 wherein said base includes an adhesive means for releasably mounting said base to a surface.

16. The retainer defined in claim 11 wherein said base comprises hinge means for hingedly pivoting said first support member relative to said second support member.

17. The retainer defined in claim 15 wherein said hinge means includes a spring means for resiliently urging said first support member toward said second support member when said hinge means is closed to a position bringing said first support member into juxtaposition with said second support member.

18. The retainer defined in claim 1 wherein said base and said first support member are identical with said second support member in spaced relationship.

19. The retainer defined in claim 1 wherein said first support member includes a novelty design.

20. A retainer comprising:
a pair of synthetic sponges;
support means for supporting said synthetic sponges in juxtaposition said support means having an abrasive member; and
securement means for attaching said support means to an object.

21. The retainer defined in claim 20 wherein said pair of synthetic sponges comprises a first synthetic sponge and a second synthetic sponge and said support means includes a hinge means for hingedly moving said first synthetic sponge relative to said second synthetic sponge.

22. The retainer defined in claim 20 wherein said support means includes a clip means for releasably holding said support means with said synthetic sponges in juxtaposition.

23. The retainer defined in claim 20 wherein said securement means comprises a flexible strap means for wrapping about said object.

24. The retainer defined in claim 20 wherein said securement means comprises an adhesive means for adhesively securing said support means to said object.

* * * * *